(12) United States Patent
Barnes et al.

(10) Patent No.: US 8,808,759 B1
(45) Date of Patent: Aug. 19, 2014

(54) STABILIZED COLLOIDAL PREPARATIONS, PRE-MIX AND PROCESS FOR PREPARING SKIN CARE COMPOSITIONS, IMPROVED SKIN CARE COMPOSITION, METHOD FOR TREATING THE SKIN

(71) Applicants: Lisa Barnes, Ooltewah, TN (US); Jason Sondgeroth, Ooltewah, TN (US); Brittany Hale, Chattanooga, TN (US)

(72) Inventors: Lisa Barnes, Ooltewah, TN (US); Jason Sondgeroth, Ooltewah, TN (US); Brittany Hale, Chattanooga, TN (US)

(73) Assignee: Chattem, Inc, Chattanooga, TN (US)

( * ) Notice: Subject to any disclaimer, the term of this patent is extended or adjusted under 35 U.S.C. 154(b) by 0 days.

(21) Appl. No.: 14/036,693

(22) Filed: Sep. 25, 2013

(51) Int. Cl.
*A61K 36/00* (2006.01)
*A61Q 19/00* (2006.01)
*A61K 8/02* (2006.01)

(52) U.S. Cl.
CPC .............. *A61K 8/0216* (2013.01); *A61Q 19/00* (2013.01); *A61Q 19/007* (2013.01)
USPC ....................................... 424/725

(58) Field of Classification Search
None
See application file for complete search history.

(56) References Cited

U.S. PATENT DOCUMENTS

| | | |
|---|---|---|
| 2,819,176 A | 1/1958 | Vartanian et al. |
| 4,309,454 A | 1/1982 | Feldstein |
| 4,597,794 A | 7/1986 | Ohta et al. |
| 4,902,442 A | 2/1990 | Garces |
| 5,085,698 A | 2/1992 | Ma et al. |
| 5,437,858 A | 8/1995 | Hungerbach et al. |
| 5,690,945 A * | 11/1997 | Bui-Bertrand et al. ....... 424/401 |
| 6,245,832 B1 | 6/2001 | Suzuki et al. |
| 6,368,579 B1 | 4/2002 | Barr |
| 6,416,788 B1 | 7/2002 | Barr |
| 8,486,463 B1 * | 7/2013 | Brieva et al. ................ 424/744 |
| 2006/0084720 A1 | 4/2006 | Tyvoll et al. |
| 2006/0102052 A1 | 5/2006 | Doles |
| 2008/0194662 A1 * | 8/2008 | Kunin ......................... 514/385 |
| 2011/0117035 A1 * | 5/2011 | Jacquinot et al. .............. 424/59 |
| 2013/0022562 A1 * | 1/2013 | Maunsell et al. .............. 424/59 |

FOREIGN PATENT DOCUMENTS

| | | |
|---|---|---|
| CA | 575194 | 5/1959 |
| CA | 677696 | 7/1964 |
| EP | 0976797 | 2/2000 |
| EP | 1666547 | 6/2006 |
| GB | 1249558 | 10/1971 |
| WO | WO 2005/097937 | 10/2005 |
| WO | WO 2009/002377 | 12/2008 |
| WO | WO 2009/127256 | 10/2009 |

* cited by examiner

*Primary Examiner* — Qiuwen Mi
(74) *Attorney, Agent, or Firm* — Serena Farquharson-Torres

(57) ABSTRACT

The present invention provides an approach for stabilizing and/or smoothing preparations containing colloidal materials, a pre-mix and a process for preparing skin care compositions and an improved skin care composition, said composition being presented in semi-solid or wet form and comprising more than 1% (w/w) of colloidal material. In one embodiment of the invention the composition comprises more than 1% of colloidal material such as colloidal oatmeal, said composition being particularly useful for treating the skin and ameliorating skin disorder symptoms.

16 Claims, No Drawings

STABILIZED COLLOIDAL PREPARATIONS, PRE-MIX AND PROCESS FOR PREPARING SKIN CARE COMPOSITIONS, IMPROVED SKIN CARE COMPOSITION, METHOD FOR TREATING THE SKIN

FIELD OF THE INVENTION

The present invention is related to pharmaceutical and/or cosmetic preparations. More specifically, the present invention provides an approach for stabilizing and/or smoothing preparations containing colloidal materials, a pre-mix and a process for preparing skin care compositions, and an improved skin care composition, said composition being presented in semi-solid or wet form and comprising more than 1% (w/w) of colloidal material. In one embodiment of the invention the composition comprises more than 1% of colloidal material such as colloidal oatmeal, said composition being particularly useful for treating the skin and ameliorating skin disorder symptoms.

BACKGROUND OF THE INVENTION

Colloidal materials dispersed in aqueous- or oil-based carriers have found application in a widespread number of areas such as pharmaceutical, cosmetic, paints, inks and agriculture, just to name a few. A colloidal material is characterized by presenting particles which are approximately 10 to 1,000 nanometers in size. A dispersion, formulation or composition comprising a colloidal material is considered stable when it successfully prevents the colloid from being easily agglomerated, coalesced or rapidly settled from the liquid or semi-solid carrier where it is dispersed.

A great amount of exploration has been made to develop and create colloidal dispersions and compositions that are stable against agglomeration, coalescence and settling. Some substances or compounds have been used as colloid stabilizers, providing increased stability to colloidal compositions against aforementioned issues. The term "colloid stabilizer" as used herein is intended to encompass agents which interacts favorably with the colloid improving its overall properties so as to abolish, prevent, delay or minimize their coalescence, coagulation and precipitation.

There are several classes of commercially important inorganic and organic colloids such as silicon dioxide, titanium dioxide and oatmeal. Therefore, numerous attempts to find efficient colloidal stabilizers for these materials have been done. For instance, documents CA 575194, CA 677696, EP 0976797, U.S. Pat. No. 4,902,442, WO 2009/127256 and US 2006/102052 relate to silica colloidal compositions stabilized by ammonia, sodium/potassium hydroxide, aluminum, siliconates, hydronium and amino alcohols, respectively. Patent document WO 2009/002377 discloses a method for making a stabilized-colloidal silica which includes forming a solution by mixing the colloidal silica with a solvent and then add one stabilizer selected from siloxans, surface active agents, polysorbates and acrylic polymer-based flow-enhancing.

Colloidal iron solutions (mainly ferric hydroxide) are shown to be stabilized by dextrin, more specifically yellow dextrin from potato starch as described by document GB 1249558. Also, a combination of ammonia, monovalent inorganic acid (e.g. HCl, HBr) and water-soluble aliphatic acids (e.g. gluconic acid) is used to stabilize colloidal titanium compositions according to patent U.S. Pat. No. 2,819,176.

Document U.S. Pat. No. 4,309,454 shows that thiourea is a great stabilizer of colloidal compositions for electroless deposition, decreasing deterioration of the colloid. An interesting feature is disclosed by patent U.S. Pat. No. 5,437,858, where the colloidal material presents stabilizing properties. In this case, colloidal silver is used to stabilize hydrogen peroxide solutions.

Patent document WO 2005/097937 is related to a colloidal system called "Aphron" and demonstrates that, in order to stabilize this system, it is necessary to have two special stabilizers, referred to as primary and secondary Aphron stabilizers.

All of these instances show that providing adequate stability to colloidal systems is not an easy task and that the efficacy of the stabilizer is dependent on its nature and properties as they have to properly align with the properties of both the colloidal material and the carrier.

The stability issue in skin care formulations that comprise both aqueous and/or oil phases has always been and continues to be a challenge for the professionals in this field, and still demands innovative solutions. Since these formulations are metastable systems, stabilization generally consists in decreasing the speed of the particle aggregation phenomena which are very common in colloids, including coalescence. Another fact that contributes for the destabilization is that some colloidal materials absorb water from the formulation but, over time, this previously absorbed water is released to the formulation, causing it to "leak" and, thus, such materials do not present adequate smoothness and/or are difficult and unpleasant to spread.

An interesting approach adopted for colloidal stabilization is the use of polymers. Polymers can present both hydrophobic and hydrophilic units, thus, can interact with the water-insoluble surface of the colloid and with the aqueous-based carrier fluid. Many polymers have been proposed as stabilizers of colloidal material. However, the surfaces of colloids vary substantially and will sometimes have dramatically different affinity for a given polymer. The use of organic co-solvents in the carrier to auxiliate the dispersion of the colloid may also have a deep impact on the affinity of the polymer for any given colloidal material. Polymers are believed to adsorb to the surface of the colloidal particles, thus promoting what is called steric stabilization. Examples that apply the aforementioned approach are described in U.S. Pat. Nos. 6,245,832; 5,085,698; and 4,597,794 for stabilization of pigments. Recently, copolymers have been designed to present a hydrophobic unit combined with multiple types of hydrophilic units, as disclosed in documents US 2006/0084720 and EP 1666547. Although these polymers are known as colloidal stabilizers for water-based carriers, they can be insufficient stabilizers of colloids in a composition constituted by water and organic phases. This seems to be the reason behind the fact that, to the best knowledge of the inventors, polymers/copolymers have never been so far considered as stabilizers of colloidal materials in topical formulations or skin care formulations. This may be a result of the property of polymers, which generally act as thickener agents and, therefore, do not promote a smoothing effect on the formulation. This limitation is particularly relevant when considering pharmaceutical and/or cosmetic compositions comprising higher levels of colloidal materials such as colloidal oatmeal (e.g. more than 10%) to provide more efficacy and protection while still being smooth and stable in solution—which were not so far available in the market.

Oatmeal has been used throughout history as a topical application for the skin in cosmetic preparations, raw and for the bath. It has been used ground dry as well as cooked. Technology now allows the extraction of certain properties from the entire oat, not just the grain. Colloidal oatmeal, a product processed by grinding of the oat grain, has been consistently recommended for adults, geriatrics and infants in lotions, creams, shampoos, conditioners, soaps, ointments and the like as well as in bath and cleansing products. Oat derived colloidal oatmeal is devised for external application to the affected area of the body by applying directly to the desired area for treating skin discomforts as well as maintaining normal skin. Colloidal oatmeal additions to skin have a soothing effect on inflammation and irritation. Colloidal oatmeal is considered safe at all concentrations as an effective agent for symptomatic relief and treatment of dry skin and the resulting itching. Colloidal oatmeal, due to its physical and chemical properties, isolates exposed skin or mucous membrane surface from harmful or annoying stimuli and, thus, falls within the topical analgesic definition of skin protectant. Oatmeal leaves behind a thin occlusive film on the skin and this serves to hold in the adsorbed water. The result of this coating is that the skin is protected against irritation and hence the ingredient has an antipruritic and generally soothing effect.

However, colloidal materials for skin care preparations, as is the case of colloidal oatmeal, are not fully soluble in aqueous solutions and tend to leave undesirable residues on the skin and other surfaces. Furthermore, liquid oat extracts prepared by extraction with alcohol, glycols, ethers, esters and mixtures thereof are typically unstable materials, which, if not emulsified, readily separate into oil and aqueous phases which may further separate into soluble and insoluble phases. Alcohol soluble cereal proteins interact with a wide range of phenolic compounds naturally found in cereal grains, forming a chill haze or protein haze. These hazes will cause the extract to become turbid. Over time, the hazes will agglomerate resulting in an insoluble precipitate. Therefore, it is clear that it is very difficult to prepare a pharmaceutical or cosmetic compositions presenting high concentration of colloidal materials such as colloidal oatmeal without compromising its long-term stability, smooth feel and effectiveness.

Document U.S. Pat. No. 6,368,579B1 describes an "oat protein complex", which comprises the colloidal oatmeal as the main active ingredient plus hydrolyzed oat protein and oat beta glucan extract as secondary active ingredients. According the aforementioned document, said complex would result in compositions presenting higher concentrations of colloidal oatmeal not often seen in other formulations, as they tend to get too thick. However, said stabilizer is different as compared to that of the present invention and the highest concentration of colloidal oatmeal presented in the formulations described in the examples of said document is 5.76% (w/w).

Patent documents US 2013/022562A1 and U.S. Pat. No. 6,416,788B1 describe formulations containing more than 40% (w/w) of colloidal oatmeal, but both are in dry loose powder form for bath dispersion purposes, not for direct application like a cream or ointment. This means that these formulations do not face the problems of stability that water-based or alcohol-based formulations do, which could not so far be stabilized if containing more than 1% (w/w) of colloidal oatmeal.

To best knowledge of the inventors, the problem of long term stability, smooth feel and effectiveness of higher concentrations of colloidal materials for skin care compositions—as is the case of colloidal oatmeal—has not been solved so far. In this context, the incorporation of more colloidal material such as oatmeal in semi-solid or "wet" pharmaceutical formulations without harming their stability and/or smooth feel is highly desirable and would increase the effectiveness of the formulation. This would also reduce the number of applications of the product through the day, thus, being extremely beneficial to the patients/users. The present invention solves these and other technical problems and further provides a direct topical formulation comprising more than 1% (w/w) of colloidal material, for skin care and/or treating skin disorders.

SUMMARY OF THE INVENTION

The present invention provides: stabilized and smooth colloidal preparations; a pre-mix for preparing skin care compositions; a process for preparing skin care compositions; an improved skin care composition; and a method for treating the skin. The inventive concept underlying these objects of the invention is the use, as stabilizing and/or smoothing agents for colloidal preparations for skin care compositions, of a polymer/copolymer system that creates microgels when is introduced to water. An embodiment of said polymer/copolymer system comprises an ionic subunit and/or multiple H-bonding sites and/or a carbon backbone comprising 12 to 20 carbon atoms. An embodiment of said polymer/copolymer system is constituted by acrylates and/or taurates such as 2-Propenoic acid, 2-hydroxyethyl ester polymer with 2-methyl-2-[(1-oxo-2-propenyl)amino]-1-propanesulfonic acid monosodium salt.

It is therefore a first object of the invention, a stabilized and smooth colloidal preparation for skin care compositions, said preparation comprising polymers/copolymers. In an embodiment, said colloidal preparation comprises colloidal oatmeal. In an embodiment, the ratio between polymers/copolymers and oatmeal ranges from 1:0.04 to 1:300. This preparation allows the incorporation of high concentrations of colloidal materials, such as oatmeal, into a water-based or alcohol-based composition yielding a long-term stable formulation featuring appropriate smoothness and thickness. In an embodiment, said stabilized colloidal preparation is used as pre-mix for preparing skin care compositions comprising more than 1% (w/w) colloidal material.

The skin care composition of the invention has improved consistency, viscosity, smoothness and stability. It is another object of the invention, a semi-solid or wet skin care composition comprising more than 1% (w/w) colloidal material and polymers/copolymers as stabilizing and/or smoothing agents. In another embodiment, the skin care composition of the invention comprises colloidal oatmeal. In another embodiment, the skin care composition of the invention comprises colloidal oatmeal up to 15% (w/w) colloidal oatmeal. In another embodiment, the skin care composition of the invention comprises:
  from 1 to 15% w/w of colloidal oatmeal;
  from 0.1 to 25% w/w of said polymer/copolymer system; and
  from 0.1 to 98.9% w/w of water and/or alcohol, optionally further comprising other pharmaceutically or cosmeceutically acceptable ingredients selected from: antioxidant; viscosity regulator; moisturizing; hydrophobic component; and combinations thereof.

The skin care composition of the invention, when comprising colloidal oatmeal, also presents anti-inflammatory, antioxidant, anti-allergic and analgesic properties. This embodiment of skin care composition of the invention is therefore useful for the protection, hydration and maintenance of healthy skin as well as for the treatment of skin disorders, discomforts and restoration of normal skin.

It is an additional object of the present invention, a process for preparing skin care compositions comprising the following steps:

adding, individually or pre-mixed to a container comprising water and/or alcohol, a colloidal material and said polymer/copolymer system, and then homogenizing the resulting mixture; and completing the volume with deionized, sterile or purified water.

In an embodiment, the process for preparing skin care compositions comprises the following steps:

adding, individually or pre-mixed to a container comprising water and/or alcohol, from 1 to 15% w/w of colloidal oatmeal and from 0.1 to 25% w/w of said polymer/copolymer system, and then homogenizing the resulting mixture; and completing the volume with deionized, sterile or purified water.

It is an additional object of the present invention a method for treating the skin, said method comprising the application, onto the skin, of a semi-solid or wet skin care composition comprising more than 1% (w/w) colloidal oatmeal and said polymers/copolymers as stabilizing and/or smoothing agents. The method of treating the skin provides protection, hydration and maintenance of healthy skin as well as the treatment of skin disorders, discomforts and restoration of normal skin because of the anti-inflammatory, antioxidant, anti-allergic and analgesic properties rendered by the skin care composition of the invention.

These and other objects of the invention will become more readily appreciated by those skilled in the art upon the detailed description below.

DETAILED DESCRIPTION OF THE INVENTION

The inventors aimed to solve the problem of long term stability, smooth feel and effectiveness of higher concentrations of colloidal material preparations for skin care compositions. Previously, both the inventors and others attempted to solve this problem by multiple approaches, but the incorporation of high concentrations of colloidal material to semi-solid or "wet" skin care pharmaceutical formulations (that is, above 1% w/w) drastically reduced their stability and/or smoothness, reducing their effectiveness and/or shelf-life. The inventors solved this technical problem by using, as stabilizing and/or smoothing agents for colloidal material preparations for skin care compositions, a polymer/copolymer system that creates microgels when is introduced to water. In an embodiment of the invention, said polymer/copolymer system comprises an ionic subunit and/or multiple H-bonding sites and/or a carbon backbone comprising 12 to 20 carbon atoms. In a further embodiment of the present invention, said polymer/copolymer system is constituted by acrylates and/or taurates. The inventors tested said polymers/copolymers as stabilizers and smoothing agents for colloidal oatmeal preparations and the results were highly unexpected as compared to other known stabilizers for skin care preparations. In the earlier attempts from the inventors, different thickening/stabilizing systems were used, but over time at room temperature water leaking out of the formulation was observed. Different ratios of waxes and emulsifiers were tried, but water was still being released from the formula over time. Once the polymer/copolymer system of the invention was developed, the preparations became completely stable with no water leaking out. If the polymer system is not used and the percentage of colloidal material such as oatmeal is 1.5% or above, the colloidal material absorbs the water in the formula and gradually releases it over time, making the formula unstable. The embodiment of a polymer/copolymer system is 2-propenoic acid, 2-hydroxyethyl ester polymer with 2-methyl-2-[(1-oxo-2-propenyl)amino]-1-propanesulfonic acid monosodium salt, for which colloidal oatmeal remains stable up to 15% (w/w).

The present invention solves the stability problem and smoothness of compositions comprising high concentrations of colloidal materials through the use of a polymer/copolymer presenting unique properties that result in more favorable interactions between the colloid, the polymer and the carrier. The polymer/copolymer can provide a composition with a wide range of viscosity and a pH range of 3-12 being suitable for use with various active ingredients and solvents. The aforementioned polymer/copolymer enhances the composition stability by creating microgels when the polymer is introduced to water, due to the polymeric chains expanding. The microgels formed work to keep the oatmeal and water in the formula trapped so that the water is not released out of the formula, thus not creating water-oil repulsion interactions and leaking water out of the formulation. The polymer/copolymer of the present invention is capable of creating said microgels due to its chemical structural features that promotes highly energetic-favored interactions with water and the colloid. Said structural features comprise subunits presenting either an ionic subunit, a number of H-bonding sites, and well-balanced carbon backbone, or a combination of both.

The present invention therefore provides: stabilized colloidal material preparations; a pre-mix for preparing skin care compositions; a process for preparing skin care compositions; an improved skin care composition; and a method for treating the skin.

In one aspect, the invention provides a stabilized colloidal material preparation for skin care compositions, said preparation comprising polymers/copolymers. The preferred ratio between polymers/copolymers and colloidal material ranges from 1:0.04 to 1:300. This preparation allows the incorporation of high concentrations of colloidal material, either individually or as a pre-mix, into a water-based or alcohol-based composition yielding a long-term stable formulation featuring appropriate smoothness and thickness.

The examples shown here are intended only to illustrate some of the many ways to carry out the invention, and should not, however, limit the scope of the same.

Process for Preparing Skin Care Compositions

The stabilized colloidal material preparation described above is used as pre-mix for preparing skin care compositions comprising more than 1% (w/w) colloidal material. In an embodiment, there is provided a process for preparing skin care compositions comprising the following steps:

adding, individually or pre-mixed to a container comprising water and/or alcohol, colloidal oatmeal and a polymer/copolymer system that creates microgels when is introduced to water, and then homogenizing the resulting mixture; and completing the volume with deionized, sterile or purified water.

In a further embodiment, the process for preparing skin care compositions comprises the following steps:

adding, individually or pre-mixed to a container comprising water and/or alcohol, from 1 to 15% w/w of colloidal oatmeal and from 0.1 to 25% w/w of a polymer/copolymer system that creates microgels when is introduced to water, and then homogenizing the resulting mixture; and completing the volume with deionized, sterile or purified water.

The prepared skin care composition has improved consistency, viscosity and stability, and when comprising colloidal oatmeal also has anti-inflammatory, antioxidant, anti-allergic and analgesic properties. The skin care composition of the invention is therefore useful for the protection, hydration and maintenance of healthy skin as well as for the treatment of skin disorders, discomforts and restoration of normal skin.

Improved Skin Care Composition

The invention further provides a semi-solid or wet skin care composition comprising a colloidal material and, as stabilizing and/or smoothing agents, a polymer/copolymer system that creates microgels when is introduced to water. In an embodiment, the skin care composition of the invention comprises more than 1% (w/w) colloidal oatmeal and polymers/copolymers as stabilizing/smoothing agents. In a further embodiment, the skin care composition of the invention comprises up to 15% (w/w) colloidal oatmeal. In another embodiment, the skin care composition of the invention comprises:
- from 1 to 15% w/w of colloidal oatmeal;
- from 0.1 to 25% of at least one polymer/copolymer, preferably 1 to 10% of one polymer or copolymer; more preferably 3 to 5% of one polymer or copolymer, the polymer/copolymer preferably being 2-propenoic acid, 2-hydroxyethyl ester polymer with 2-methyl-2-[(1-oxo-2-propenyl)amino]-1-propanesulfonic acid monosodium salt;
- the remaining volume being completed with aqueous-based or alcohol-based vehicle, preferably deionized, sterile or purified water.

Optionally, other pharmaceutically or cosmeceutically acceptable ingredients may be present in the composition in order to achieve an incremental stability and/or effect. The term "cosmeceutical" is to be herein understood as any cosmetic preparation presenting any therapeutic effect. Accordingly, "cosmeceutically" acceptable ingredients include all ingredients acceptable for cosmetic and/or pharmaceutical preparations.

One or more antioxidant agents may be optionally added to the composition, preferably 0.1 to 30% w/w of one antioxidant agent, more preferably 0.1 to 5% w/w of one antioxidant agent. An antioxidant agent can be BHT, Magnesium Ascorbyl Phosphate, Tocopheryl Acetate, *Camellia sinensis* Leaf Extract, Ascorbic Acid, *Avena sativa* (Oat) Kernel Extract, *Citrus unshiu* Fruit Extract, Ubiquinone or Ginger Root Extract.

One or more viscosity regulator agents may be optionally added to the composition, preferably 0.1 to 10% w/w of one viscosity regulator agent, more preferably 0.1 to 7% w/w of one viscosity regulator agent. A viscosity regulator can be Cetyl Alcohol, Cetearyl Alcohol, Stearyl Alcohol, Glyceryl Stearate or C10-30 Cholesterol/Lanosterol Esters.

One or more moisturizing components may be optionally added to the composition, preferably 0.1 to 5% w/w of one moisturizing component, more preferably 0.1 to 3% w/w of one moisturizing component. Moisturizing components can be *Aloe barbadensis* leaf extract, *Avena sativa* (Oat) kernel extract, *Citrus limon* (Lemon) Peel Extract, Jojoba Esters, Mineral Oil, *Camellia sinensis* Leaf Extract, Hydroxyethyl Urea, Cocodimonium Hydroxypropyl Hydrolyzed Rice Protein, Cocodimonium Hydroxypropyl Silk Amino Acids, Cholesterol, Ceramide NP, Ceramide NS, Ceramide EOS, Ceramide EOP, Ceramide AP, Caprooyl Sphingosine, Caprooyl Phytospingosine, Petrolatum, *Lavandula angustifolia* (Lavender) Extract, *Saccharum officinarum* (Sugar Cane) Extract, *Citrus aurantium dulcis* (Orange) Extract, *Pyrus malus* (Apple) Extract, *Butryospermum parkii* (Shea Butter) Extract, *Persea gratissima* (Avocado) Butter, Caprylyl Methicone, *Simmondsia chinensis* (Jojoba) Butter, *Theobroma cacao* (Cocoa) Butter, *Boswellia serrata* Gum, Caprylic/Capric Triglycerides or Amino Peptide Complex.

An hydrophobic component may be optionally added to the composition, preferably 0.1 to 40% w/w of one hydrophobic component, more preferably 0.1 to 10% w/w of one hydrophobic component. In an embodiment, the hydrophobic component is Bisabolol.

Method for Treating the Skin: Treatment of Eczema and Other Skin Disorders

The method for treating the skin comprises the application, onto the skin, a semi-solid or wet skin care composition comprising a colloidal material and polymers/copolymers as stabilizing/smoothing agents. In an embodiment the method for treating the skin comprises the application, onto the skin, a semi-solid or wet skin care composition comprising more than 1% (w/w) colloidal oatmeal and polymers/copolymers as stabilizing agents. This method of treating the skin provides protection, hydration and maintenance of healthy skin as well as the treatment of skin disorders, discomforts and restoration of normal skin because of the anti-inflammatory, antioxidant, anti-allergic and analgesic properties rendered by the skin care composition of the invention.

An embodiment of the composition of the invention is shown in table 1 below. This composition is a topically applied formulation having multiple simultaneous effects, i.e. anti-inflammatory, antioxidant, anti-allergic, analgesic, skin protectant, protective barrier, anti-itch, burn relief and antipruritic properties featuring optimized consistency, viscosity and stability.

TABLE 1

One embodiment of a composition of the invention

| Ingredient | % w/w |
|---|---|
| Colloidal oatmeal | 5 |
| 2-Propenoic acid, 2-hydroxyethyl ester polymer with 2-methyl-2-[(1-oxo-2-propenyl)amino]-1-propanesulfonic acid monosodium salt | 5 |
| ginger root extract | 0.02 |
| C10-30 Cholesterol/Lanosterol Ester | 3 |
| Amino Peptide Complex | 1 |
| Bisabolol | 2 |
| Water | q.s.p. |

Multiple tests were performed with this composition of the invention, said tests being summarized in the tables below. Note the substantial % change after just after 1 hour of application, as reported by users.

In these studies, data was collected through Investigator Assessment, Subject Assessment, non-invasive TEWL measurement, and corneometry. The Investigator Assessment was performed immediately after the product was applied, after 15 minutes, 1 hour, 24 hours, 1 week, 2 weeks, and 4 weeks. The investigator evaluated irritation, erythema, desquamation, roughness, dryness, and overall skin appearance. The following ordinal grading scale was used: =none, 1=minimal, 2=mild, 3=moderate, 4=severe. The Subject Assessment was performed immediately after the product was applied, after 15 minutes, 1 hour, 24 hours, 1 week, 2 weeks, and 4 weeks. The subject evaluated irritation, redness, itching, discomfort, and overall skin appearance. The following ordinal grading scale was used: =none, 1=minimal, 2=mild, 3=moderate, 4=severe. A non-invasive TEWL (transepidermal water loss) measurement was taken using an evaporimeter which measures quantity of water that passes from inside a body through the epidermal layer of the skin to the surrounding atmosphere via diffusion and evaporation processes. Compromised skin (such as skin afflicted with eczema) has increased TEWL and the purpose of measuring the TEWL during this study was to determine if the test formula reduced it, showing improved skin barrier function. A baseline TEWL measurement was taken at the beginning of the study with additional measurements taken at 1 hour, 24 hours, 1 week, 2 weeks, and 4 weeks. Corneometry measurements were also taken which measure the moisture content in the epidermal layer of the skin. The purpose of these measurements in the study was to see if the test formula would increase the moisture in the skin of the subjects. A baseline corneometer measurement was taken at the beginning of the study with additional measurements taken at 1 hour, 24 hours, 1 week, 2 weeks, and 4 weeks.

The Mann-Whitney two tailed paired statistical test was used to analyze the nonparametric data gathered from the investigator and subject assessments. Nonparametric data is data that has a ranking but no clear numerical interpretation, such as when assessing preferences. In this study, the Mann-Whitney test was used to compare the data for the non-treated control site and the treated site of the each subject to determine if there was a systematic difference between the two. The Mean A listed in the tables is the mean of the data of the treated site of the subjects while Mean P is the mean of the data of the untreated site of the subjects.

The T-test two tailed paired statistical test was used to analyze the data gathered from the TEWL and corneometer measurements. This test is used when there is "before" and "after" normally-distributed data to determine if there is a significant difference between the values. In this study, the T-test was used to compare the data for the non-treated control site and the treated site of the each subject to determine if there was a systematic difference between the two. The Mean A listed in the tables is the mean of the data of the treated site of the subjects while Mean P is the mean of the data of the untreated site of the subjects.

TABLE 2

Analysis of Oatmeal Moisturizer Efficacy in Eczema. Corneometry Longitudinal Comparison. Baseline (control) parameters compared with application after 1 hour, 24 hours, 1 week, 2 weeks and 4 weeks of application.

| Subject # | Unblind | Baseline | 1 hour | 24 hours | 1 week | 2 weeks | 4 weeks |
|---|---|---|---|---|---|---|---|
| T-test two tailed paired | Mean A | 77.34 | 133.10 | 133.08 | 127.90 | 156.50 | 170.10 |
| | Baseline A | | 77.34 | 77.34 | 77.34 | 77.34 | 77.34 |
| | % Change | | 72% | 72% | 65% | 102% | 120% |
| | A v. Baseline p = | | <.001 | <.001 | <.001 | <.001 | <.001 |
| | Mean P | 78.54 | 99.62 | 97.84 | 99.19 | 99.19 | 112.81 |
| | Baseline P | | 78.54 | 78.54 | 78.54 | 78.54 | 78.54 |
| | % Change | | 27% | 25% | 3% | 26% | 44% |
| | P v. Baseline p = | | <.001 | <.001 | 0.582 | <.001 | <.001 | n = 50 patients.

Further tests with users of the composition of the invention show the smoothing effect introduced by the polymer or copolymer. The smoothness of a composition directly affects its texture and the sensation associated with the application of the product, thus, the smoothness increase promoted by the polymer or copolymer enhances the experience of the patient with the product and, consequently, enhances the compliance with the treatment. In this regard, the user's clearly felt "pleasant texture" as shown in the responses of Table 4.

TABLE 3

Analysis of Oatmeal Moisturizer Efficacy in Eczema. Baseline (control) parameters compared with immediate (t = 0) application (t = 0 min), after 15 minutes, 1 hour, 24 hours and 1 week of application.

| | | Baseline | | | | | | Immediate | | | | | |
|---|---|---|---|---|---|---|---|---|---|---|---|---|---|
| Subject # | Unblind | Irritation | Erythema | Desquamation | Roughness | Dryness | Overall | Irritation | Erythema | Desquamation | Roughness | Dryness | Overall |
| Mann-Whitney Two tailed paired | Mean A | | | | | | | −0.16 | −0.16 | −1.06 | −1.12 | −1.12 | −0.96 |
| | Mean P | | | | | | | 0.00 | −0.06 | −0.08 | −0.08 | −0.08 | −0.06 |
| | Av. P p = | | | | | | | 0.005 | 0.021 | <.001 | <.001 | <.001 | <.001 |
| | Z-score = | | | | | | | −2.84 | −2.31 | −8.37 | −8.33 | −8.33 | −8.26 |

| | | 15 min | | | | | | 1 hour | | | | | |
|---|---|---|---|---|---|---|---|---|---|---|---|---|---|
| Subject # | Unblind | Irritation | Erythema | Desquamation | Roughness | Dryness | Overall | Irritation | Erythema | Desquamation | Roughness | Dryness | Overall |
| Mann-Whitney Two tailed paired | Mean A | −0.16 | −0.16 | −1.34 | −1.44 | −1.40 | −1.16 | −0.26 | −0.24 | −1.58 | −1.60 | −1.62 | −1.38 |
| | Mean P | 0.00 | 0.00 | −0.06 | −0.06 | −0.06 | −0.06 | 0.00 | 0.00 | −0.08 | −0.08 | −0.08 | −0.06 |
| | Av. P p = | 0.005 | 0.005 | <.001 | <.001 | <.001 | <.001 | <.001 | <.001 | <.001 | <.001 | <.001 | <.001 |
| | Z-score = | −2.84 | −2.84 | −8.44 | −8.43 | −8.43 | −8.48 | −3.77 | −3.60 | −8.35 | −8.35 | −8.36 | −8.28 |

| | | 24 hours | | | | | | 1 week | | | | | |
|---|---|---|---|---|---|---|---|---|---|---|---|---|---|
| Subject # | Unblind | Irritation | Erythema | Desquamation | Roughness | Dryness | Overall | Irritation | Erythema | Desquamation | Roughness | Dryness | Overall |
| Mann-Whitney | Mean A | −1.02 | −1.04 | −1.84 | −1.88 | −1.92 | −1.72 | −1.64 | −1.62 | −2.08 | −2.12 | −2.14 | −2.06 |

TABLE 3-continued

Analysis of Oatmeal Moisturizer Efficacy in Eczema. Baseline (control) parameters compared with immediate (t = 0) application (t = 0 min), after 15 minutes, 1 hour, 24 hours and 1 week of application.

| Two tailed paired | Mean P | −0.04 | −0.04 | −0.08 | −0.10 | −0.10 | −0.12 | −0.06 | −0.06 | −0.10 | −0.14 | −0.16 | −0.18 |
|---|---|---|---|---|---|---|---|---|---|---|---|---|---|
| | A v. P p = | <.001 | <.001 | <.001 | <.001 | <.001 | <.001 | <.001 | <.001 | <.001 | <.001 | <.001 | <.001 |
| | Z-score = | −5.99 | −6.13 | −8.42 | −8.53 | −8.55 | −8.46 | −6.43 | −6.39 | −8.05 | −8.08 | −8.08 | −7.93 | n = 50 patients.

TABLE 4

Efficacy parameters of the oatmeal composition of the invention according to users/patients agreement. n = 50 patients

| RESPONDENT # | Strongly agree (%) | Agree (%) |
|---|---|---|
| Is easy to use | 94 | 100 |
| Is safe to use | 96 | 100 |
| Does not have any side effects | 83 | 90 |
| Relieves the itch of eczema | 67 | 90 |
| Is a high quality product | 79 | 94 |
| Relieves dryness | 83 | 96 |
| Relieves skin irritation | 71 | 94 |
| Is made by a brand I trust | 79 | 88 |
| Has a pleasant texture | 92 | 100 |
| Relieves skin discomfort | 83 | 100 |
| Is hypo-allergenic | 75 | 83 |
| Relieves flaking/scaly skin | 81 | 96 |
| Relieves redness | 73 | 85 |
| Moisturizes the skin | 90 | 96 |
| Works quickly | 77 | 94 |
| Improves the appearance of skin affected by eczema | 67 | 79 |
| Relieves skin inflammation | 54 | 85 |
| Heals the skin | 60 | 83 |
| Provides long lasting itch relief | 69 | 88 |
| Is more effective than other products that treat eczema | 40 | 79 |
| Allows you to use prescription remedies less often | 46 | 60 |
| Is good to use on other types of skin itches besides eczema | 58 | 79 |
| Increases you ability to wear clothes you like | 52 | 73 |
| Is the only lotion I need to use to take care of my eczema | 52 | 75 |
| Treats the underlying cause of eczema | 40 | 63 |

Those skilled in the art will readily appreciate the teachings herein provided, and will be enabled to reproduce the invention according to the examples shown above or in other embodiments, which shall be deemed as within the scope of the invention and of the appended claims.

The invention claimed is:

1. A stabilized colloidal non-extruded oatmeal preparation for water-based skin care composition comprising, as stabilizer and smoothing agent, from 0.1 to 15% w/w of a polymer/copolymer system comprising 2-methyl-2-[(1-oxo-2-propenyl)amino]-1-propanesulfonic acid monosodium salt.

2. The stabilized preparation according to claim 1 wherein the concentration of non-extruded colloidal oatmeal is within the range of 2% (w/w) to 15% (w/w).

3. The stabilized preparation according to claim 2 wherein the concentration of non-extruded colloidal oatmeal is above 10% (w/w).

4. A pre-mix for preparing water-based skin care composition comprising, non-extruded colloidal oatmeal as stabilizer and smoothing agent, from 0.1 to 15% w/w of a polymer/copolymer system presenting at least a taurate.

5. The pre-mix according to claim 4 wherein the concentration of non-extruded colloidal oatmeal is within the range of 2% (w/w) to 15% (w/w).

6. The pre-mix according to claim 5 wherein the concentration of non-extruded colloidal oatmeal is above 10% (w/w).

7. A water based skin care composition comprising:
a non-extruded colloidal oatmeal;
at least one stabilizer and smoothing agent consisting of a polymer/copolymer system comprising taurate; and
water and/or alcohol, optionally further comprising other pharmaceutically or cosmeceutically acceptable ingredients selected from the group consisting of: antioxidant; viscosity regulator; moisturizing; hydrophobic component; and combinations thereof.

8. The skin care composition according to claim 7 comprising:
more than 10% w/w of non-extruded colloidal oatmeal;
from 0.1 to 15% w/w of said polymer/copolymer system; and
optionally further comprising other pharmaceutically or cosmeceutically acceptable ingredients selected from: antioxidant; viscosity regulator; moisturizing; hydrophobic component; and combinations thereof.

9. The skin care composition according to claim 8, wherein said antioxidant agent is selected from BHT, magnesium ascorbyl phosphate, tocopheryl acetate, *Camellia sinensis* leaf extract, ascorbic Acid, oat kernel extract, *Citrus unshiu* fruit extract, ubiquinone, ginger root extract, or combinations thereof.

10. The skin care composition according to claim 8, wherein said viscosity regulator is selected from cetyl alcohol, cetearyl alcohol, stearyl alcohol, glyceryl stearate, C10-30 cholesterol/lanosterol esters, or combinations thereof.

11. The skin care composition according to claim 8, wherein said moisturizing component is selected from *Aloe barbadensis* leaf extract, oat kernel extract, lemon peel extract, jojoba esters, mineral oil, *Camellia sinensis* leaf extract, hydroxyethyl urea, cocodimonium hydroxypropyl hydrolyzed rice protein, cocodimonium hydroxypropyl silk amino acids, cholesterol, ceramide nonhydroxy fatty acid phytosphingosine, ceramide nonhydroxy fatty acid sphingosine, ceramide ester-linked sphingosine, ceramide ester-linked phytosphingosine, ceramide α-hydroxy fatty acid phytosphingosine, caprooyl sphingosine, caprooyl phytosphingosine, petrolatum, lavender extract, sugar cane extract, orange extract, apple extract, shea butter extract, avocado butter, caprylyl methicone, jojoba butter, cocoa butter, *Boswellia serrata* gum, caprylic/capric triglycerides, amino peptide complex, or combinations thereof.

12. The skin care composition according to claim 8, wherein said hydrophobic component is bisabolol.

13. A skin care composition consisting of: 5% colloidal oatmeal; 5% 2-propenoic acid, 2-hydroxyethyl ester polymer with 2-methyl-2-[(1-30 oxo-2-propenyl)amino]-1-propanesulfonic acid monosodium salt; 0.02% ginger root extract; 3% C10-30 cholesterol/lanosterol ester; 1% amino peptide complex; 2% bisabolol and water to complete 100% (w/w).

14. A process for preparing skin care compositions comprising the following steps:
- adding, individually or pre-mixed to a container comprising water and/or alcohol, a colloidal non-extruded oatmeal and, as stabilizer and smoothing agent, from 0.1 to 15% w/w of a polymer/copolymer system comprising a taurate, and then homogenizing the resulting mixture; and
- completing the volume with deionized, sterile or purified water.

15. The process according to claim 14 comprising the following steps:
- adding, individually or pre-mixed to a container comprising water and/or alcohol, from 2 to 15% w/w of colloidal oatmeal and from 0.1 to 15% w/w of said polymer/copolymer system, and then homogenizing the resulting mixture; and
- completing the volume with deionized, sterile or purified water.

16. Process according to claim 15 further comprising the incorporation of ingredients selected from: antioxidant; viscosity regulator; moisturizing; hydrophobic component; and combinations thereof.

* * * * *